United States Patent [19]

Eastman

[11] Patent Number: 5,003,082

[45] Date of Patent: Mar. 26, 1991

[54] PREPARATION OF THIOLACTAMS

[75] Inventor: Alan D. Eastman, Bartlesville, Okla.

[73] Assignee: Phillips Petroleum Company, Bartlesville, Okla.

[21] Appl. No.: 501,693

[22] Filed: Mar. 29, 1990

[51] Int. Cl.[5] .................. C07D 201/00; C07D 207/267
[52] U.S. Cl. .................................................... 548/543
[58] Field of Search ......................... 548/543; 546/243

[56] References Cited

U.S. PATENT DOCUMENTS

| | | | |
|---|---|---|---|
| 3,050,472 | 8/1962 | Morrell | 252/435 |
| 3,105,101 | 9/1963 | Evans | 260/679 |
| 3,306,910 | 2/1967 | Louthan | 260/326.83 |
| 3,306,911 | 2/1967 | Doss | 548/543 |
| 3,344,166 | 9/1967 | Zinsstag | 260/465.2 |
| 3,632,605 | 1/1972 | Debarre | 548/543 |
| 4,145,352 | 3/1979 | Kubicek | 260/326.82 |
| 4,757,143 | 7/1988 | Vanderpool et al. | 544/352 |

*Primary Examiner*—David B. Springer
*Attorney, Agent, or Firm*—K. K. Brandes

[57] ABSTRACT

The reaction of lactams (preferably N-methyl-2-pyrrolidone) with hydrogen sulfide to thiolactams (preferably N-methyl-2-thiopyrrolidone) is conducted in the presence of a catalyst comprising an inorganic support material and a phosphorus and oxygen containing compounds.

16 Claims, No Drawings

PREPARATION OF THIOLACTAMS

BACKGROUND OF THE INVENTION

This invention relates to the catalytic conversion of hydrogen sulfide and lactams (cyclic amides) to thiolactams. In a particular aspect, this invention relates to the catalytic reaction of N-methyl-2-pyrrolidone with hydrogen sulfide to N-methyl-2-thiopyrrolidone (also referred to as N-methylpyrrolidine-2-thione).

The catalytic conversion of lactams (in particular N-methyl-2-pyrrolidone) and $H_2S$ to thiolactams (in particular N-methyl-2-thiopyrrolidone) is known and has been described in U.S. Pat. No. 4,145,352, the entire disclosure of which is incorporated herein by reference. As has been pointed out in this patent, N-methyl-2-thiopyrrolidone can be used as a sulfur source in the preparation of poly(phenylene sulfide). The instant invention is directed to an improvement of the process of U.S. Pat. No. 4,145,352 by employing a more effective catalyst.

SUMMARY OF THE INVENTION

It is an object of this invention to prepare thiolactams by the catalytic reaction of lactams with hydrogen sulfide. It is another object of this invention to prepare N-methyl-2-thiopyrrolidone from N-methyl-2-pyrrolidone and $H_2S$. Other objects and advantages will become apparent from the detailed disclosure and the appended claims.

In accordance with this invention, in a process for reacting at least one lactam with hydrogen sulfide so as to produce at least one thiolactam, the improvement comprises employing a catalyst comprising an inorganic support material and at least one phosphorus and oxygen containing compound deposited on said support material, wherein molybdenum and tungsten are substantially absent.

DETAILED DESCRIPTION OF THE INVENTION

Any suitable lactam (cyclic amide) can be employed as reactant in the process of this invention. These lactams are represented by the structural formula:

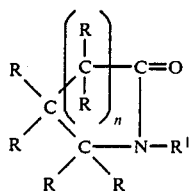

wherein each R and $R^1$ is independently selected from the group consisting of hydrogen, alkyl radicals and cycloalkyl radicals, and combinations thereof, preferably containing from 1 to 6 carbon atoms; and n can be an integer in the range of from 0 to 10. The total number of carbon atoms in these lactams generally should not exceed 20.

Lactams which can be converted to thiolactams by the process of this invention include 2-azetidinone, 2-pyrrolidone, 2-piperidone, 2-oxohexamethylenimine(-caprolactam), N-methyl-2-azetidinone, N-methyl-2-pyrrolidone, N-ethyl-2-pyrrolidone, N-propyl-2-pyrrolidone, 2-oxo-1-ethylhexamethylenimine, 3,3-di-n-propyl-2-piperidone, 2-oxo-4-n-hexyl-hexamethylenimine, 2-oxo-2-cyclopentylhexamethylenimine, lactam of 7-(cyclohexylamino)-heptanoic acid, lactam of 13-aminotridecanoic acid, 3,4,5-tri-n-pentyl-2-piperidone, 3-cyclopentyl-2-pyrrolidone, lactam of 3-amino-3-cyclohexyl-4-ethyloctanoic acid, 1-isopropyl-2-pyrrolidone, 2-oxo-1-ethyl-3-tert-butylhexamethylenimine, and the like. Preferred lactams are N-alkyl-2-pyrrolidones with the alkyl group containing 1-3 carbon atoms; in particular N-methyl-2-pyrrolidone.

The thiolactams which are prepared by the process of this invention are represented by the formula:

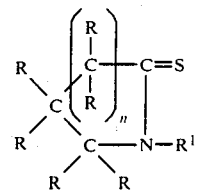

wherein R, $R^1$ and n are as defined above (for lactams).

The preferred thiolactams are N-alkyl-2-thiopyrrolidones with the alkyl group containing 1-3 carbon atoms, in particular N-methyl-2-thiopyrrolidone.

The inorganic support material of the catalyst employed in the process of this invention can be any suitable solid inorganic material, preferably selected from the groups consisting of boria, alumina, silica, diatomite (kieselgur), aluminosilicates (such as clays or zeolites), yttrium oxide, oxides of lanthanides, titania, zirconia, hafnia, vanadia, niobium oxide, tantalum oxide, activated carbon, and the like, mixtures of two or three of the above materials, and combinations of the above materials with an oxide of alkali metals and/or alkaline earth metal. Particularly preferred support materials are diatomite, activated carbon, and lithium oxide on titania (more preferably with a lithium content of about 1-25 weight-%). Detailed descriptions of the most preferred support materials are provided in Example I.

The surface area (determined by the BET method employing $N_2$; substantially in accordance with ASTM D3037) of the inorganic support material should exceed about 10 $m^2/g$, and generally is in the range of from about 10 to about 300 $m^2/g$. The inorganic support particles can have spherical, trilobal, quadrilobal or cylindrical shape. Impurities should be substantially absent from the support material (i.e., they should not be present at a level higher than about 0.5, and should preferably be less than about 0.2 weight-%).

The phosphorus and oxygen containing component of the catalyst employed in the process of this invention can be any suitable acidic P-O containing compounds, preferably selected from the group consisting of phosphoric acid (i.e., orthophosphoric acid and/or pyrophosphoric acid and/or metaphosphoric acid and/or polyphosphoric acid), ammonium dihydrogen phosphate, diammonium hydrogen phosphate, alkali metal dihydrogen phosphate, dialkali metal hydrogen phosphate, phosphorous acid, ammonium dihydrogen phosphite, alkali metal dihydrogen phosphite, and the like, and mixtures thereof. Presently preferred phosphorus and oxygen containing compounds are phosphoric acid and $(NH_4)_2HPO_4$.

The catalyst which is used in the process of this invention can be prepared by any suitable means. Generally, the inorganic support material is impregnated with a solution (preferably aqueous) of at least one phosphorus and oxygen containing compound, e.g., by incipient wetness impregnation or by spraying the solution onto the support material. The concentration of the P and O containing compound in the solution and the weight ratio of the solution to the support material are chosen such as to provide a weight percentage of phosphorus in the finished catalyst in the range of about 0.5 to about 25 weight-% P, preferably about 2-12 weight-% P. Thereafter, the material is heated at a temperature high enough (preferably about 400°-700° C.) so as to substantially dry the catalyst composition. If an acidic ammonium salt of phosphoric acid or phosphorus acid is employed, some ammonia may be released during this heating step. The surface area and shape of the finished catalyst is approximately the same as the surface area and shape of the support material (described above). Mo and W are to be substantially absent (i.e., these elements should not be present in the catalyst at amounts above about 0.1 weight-%).

The reaction conditions for the catalytic preparation of thiolactams described herein are considered to be mild. Generally, the reaction is carried out at an elevated temperature of about 500°-800° F., with a preferred range of about 500° to about 700° F. (about 260°-371° C.). The reaction can be carried out at a pressure ranging from about 1 to about 1000 psia, with a preferred pressure range of about 7 to about 150 psia (about 0.5-10 atm).

Although the invention is operable over a broad range of molar ratios of the reactants and with a broad range of feed rates, the usual range of the molar ratio of $H_2S$ to lactam in the feed is about 2:1 to about 20:1, with a preferred range of about 3:1 to about 12:1. It is understood that $H_2S$ and lactam can be introduced simultaneously but separately into the reaction zone, or they can be introduced admixed in one feed stream. The weight hourly space velocity of the lactam will generally be in the range of from about 1 to about 2000 g lactam/g catalyst/hour, preferably about 2-200 g/g/hour.

The formed thiolactam can be separated from unconverted reactants (lactam and $H_2S$) and from by-products, such as water (which is also formed in the reaction), by any suitable separating means, such as fractional distillation, and can then be recovered. Uncoverted lactam and $H_2S$ can be recycled to the reaction zone. The reaction of this invention and the subsequent separation steps can be carried out as batch operations or continuously (the latter being preferred).

The following example is presented in further illustration of the invention and are not to be considered as unduly limiting the scope of this invention.

EXAMPLE

This example illustrates the reaction of N-methyl-2-pyrrolidone (NMP) with $H_2S$ to N-methyl-2-thiopyrrolidone (TNMP) and water, in the presence of supported P/O-containing catalysts.

A tubular stainless steel reactor of 80 cc internal volume was charged with a support layer of inert α-alumina (Alundum ®; surface area: about 1 $m^2/g$), a layer of 10 cc of a catalyst, and a top layer of Alundum ®. The reactor was heated to the desired reaction temperature by means of a three-zone electrical furnace. $H_2S$ gas was introduced through an inlet tube at the reactor top, generally at a gas hourly space velocity (GHSV) of about 1,800-2,500 cc $H_2S$ per cc catalyst. Liquid NMP was introduced through another inlet tube at the reactor top, generally at a weight hourly space velocity of about 3-10 g NMP per g catalyst per hour. The gaseous effluent was analyzed by means of a gas chromatograph.

The following catalyst were tested:

(A) Phosphoric Acid on Kieselgur (diatomite), had been provided by United Catalyst Incorporated, Louisville, Ky. Catalyst A contained about 7 weight-% P.

(B) Phosphorus on Activated Carbon was prepared as follows:

13.4 grams of 12-40 mesh WV-G Nuchar activated carbon was impregnated with 13.4 grams of $NH_4)_2HPO_4$, dissolved in enough water to dissolve it. The thus-impregnated material was dried and then calcined in air at about 600° C. for about 3 hours. Calcined Catalyst B contained about 7 weight-% P.

(C) Phosphorus on Lithium Oxide/Titania was prepared as follows:

First, a solution of 136 g $Li_2CO_3$ in 1 liter of distilled water was mixed with an aqueous slurry of 500 grams $TiO_2$. The obtained wet mixture of $Li_2CO_3$ and $TiO_2$ was dried in a heated oven for about 16 hours and then calcined at 800° C. for 3 hours. 38.9 g of the calcined material (probably mixed oxides of Li and Ti) was impregnated with 25.0 grams of an aqueous solution of $(NH_4)_2 HPO_4$ dissolved in a sufficient amount of water to dissolve it. The thus-impregnated material was dried and then calcined in air at about 600° C. for about 3 hours. Calcined Catalyst C contained about 7 weight-% P and about 5 weight-% Li.

(D) Catalyst in accordance with U.S. Pat. No. 4,145,352, comprising 5 weight-% phosphotungstic acid on alumina.

TABLE

| Catalyst | Average Reaction Temp. (° F.) | Average Pressure (psia) | Average GHSV of $H_2S$ | Average Molar Ratio of $H_2S$/NMP | Average Conversion of NMP (%) | Average Selectivity to TNMP (%)[5] |
|---|---|---|---|---|---|---|
| A[1] (Invention) | 630 | 14.4 | 2360 | 7.9:1 | 10.8 | 98.9 |
| B[2] (Invention) | 650 | 14.6 | 2490 | 5.2:1 | 14.5 | 97.6 |
| C[3] (Invention) | 620 | 14.8 | 2350 | 7.2:1 | 26.1 | 98.9 |
| D[4] (Control) | 725 | 17.1 | 2070 | 5.0:1 | 7.8 | 79.2 |

[1] average of 5 measurements during 69 hours on stream
[2] average of 20 measurements during 113 hours on stream
[3] average of 5 measurements during 47 hours on stream
[4] average of 5 measurements during 43 hours on stream
[5] calculated on a water-free basis The test results in the Table clearly show the unexpected superiority of the three invention catalysts A, B and C versus the catalyst of U.S. Pat. No. 4,145,352 (phosphotungstic acid on alumina). Catalyst C (P on Li/Ti-oxide) was the most active and selective catalyst.

Reasonable variations and modifications are possible within the scope of the disclosure of this invention and the appended claims.

That which is claimed is:

1. In a process for catalytically reacting at least one lactam with hydrogen sulfide so as to produce at least one thiolactam, the improvement which comprises employing a catalyst comprising (a) an inorganic support material and (b) at least one phosphorus and oxygen containing compound deposited on said support material, wherein molybdenum and tungsten are substantially absent from said catalyst, and wherein said at least one phosphorus and oxygen containing compound is selected from the group consisting of phosphoric acid, ammonium dihydrogen phosphate, diammonium hydrogen phosphate, alkali metal dihydrogen phosphate, dialkali metal hydrogen phosphate, phosphorous acid, ammonium dihydrogen phophite, alkali metal dihydrogen phosphite, and mixtures thereof.

2. A process in accordance with claim 1, wherein said inorganic support material is selected from the group consisting of boria, alumina, silica, diatomite, aluminosilicates, yttrium oxide, oxides of lanthanides, titania, zirconia, hafnia, vanadia, niobium oxide, tantalum oxide, activated carbon, and mixtures thereof.

3. A process in accordance with claim 2, wherein said inorganic support material further contains at least one oxide of at least one metal selected from the group consisting of alkali metals and alkaline earth metals.

4. A process in accordance with claim 1, wherein said catalyst has a surface area, determined by the BET method employing $N_2$, in excess of about 10 $m^2/g$.

5. A process in accordance with claim 1, wherein said at least one lactam is a N-alkyl-2-pyrrolidone with the alkyl group containing 1-3 carbon atoms, and the thiolactam is a N-alkyl-2-thiopyrrolidone with the alkyl group containing 1-3 carbon atoms.

6. In a process for catalytically reacting N-methyl-2-pyrrolidone with hydrogen sulfide so as to produce N-methyl-2-thiopyrrolidone, the improvement which comprises employing a catalyst comprising (a) an inorganic support material and (b) at least one phosphorus and oxygen containing compound deposited on said support material, wherein molybdenum and tungsten are substantially absent from said catalyst, and wherein said at least one phosphorus and oxygen containing compound is selected from the group consisting of phosphoric acid, ammonium dihydrogen phosphate, diammonium hydrogen phosphate, alkali metal dihydrogen phosphate, dialkali metal hydrogen phosphate, phosphorous acid, ammonium dihydrogen phosphite, alkali metal dihydrogen phosphite, and mixtures thereof.

7. A process in accordance with claim 6, wherein said inorganic support material is selected from the group consisting of diatomite, lithium oxide on titania, and activated carbon.

8. A process in accordance with claim 6, wherein said at least one phosphorus and oxygen compound is phosphoric acid or diammonium hydrogen phosphate.

9. A process in accordance with claim 6, wherein the surface area of said catalyst, determined in accordance with the BET method employing $N_2$, exceeds about 10 $m^2/g$.

10. A process in accordance with claim 6, wherein said catalyst contains about 0.5-25 weight-% phosphorus and said inorganic support material is diatomite.

11. A process in accordance with claim 6, wherein said catalyst contains about 0.5-25 weight-% phosphorus, and said inorganic support material comprises lithium oxide on titania.

12. A process in accordance with claim 11, wherein the lithium content in said inorganic support material is about 1-25 weight-% Li.

13. A process in accordance with claim 6, wherein said process is carried out at a temperature of about 500°-800° F. and a molar ratio of $H_2S$ to N-methyl-2-pyrrolidone of about 2:1 to about 20:1.

14. A process in accordance with claim 13, wherein said temperature is about 600°-750° F. and said molar ratio is about 3:1 to about 12:1.

15. A process in accordance with claim 13, wherein said process is carried out at a weight hourly space velocity of N-methyl-2-pyrrolidone of about 2,000 g per gram catalyst per hour and a pressure of about 1 to about 1,000 psia.

16. A process in accordance with claim 6, wherein said N-methyl-2-thiopyrrolidone is recovered after having been separated from unconverted N-methyl-2-pyrrolidone, unconverted $H_2S$ and formed water.

* * * * *